(12) United States Patent
Parins

(10) Patent No.: US 7,833,175 B2
(45) Date of Patent: Nov. 16, 2010

(54) MEDICAL DEVICE COIL

(75) Inventor: David J. Parins, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1587 days.

(21) Appl. No.: 10/656,418

(22) Filed: Sep. 5, 2003

(65) Prior Publication Data
US 2005/0054950 A1    Mar. 10, 2005

(51) Int. Cl.
*A61M 25/00* (2006.01)
*A61M 5/178* (2006.01)

(52) U.S. Cl. .................. 600/585; 604/164.13; 604/524

(58) Field of Classification Search ................ 600/585; 604/164.13, 524
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 3,789,841 A | 2/1974 | Antoshkiw | |
| 4,538,622 A | 9/1985 | Samson et al. | |
| 4,554,929 A | 11/1985 | Samson et al. | |
| 4,619,274 A | 10/1986 | Morrison | |
| 4,714,815 A | 12/1987 | Swarts et al. | |
| 4,721,117 A | 1/1988 | Mar et al. | |
| 4,763,647 A | 8/1988 | Gambale | |
| 4,846,186 A | 7/1989 | Box et al. | |
| 4,955,862 A | 9/1990 | Sepetka | |
| 4,966,163 A | 10/1990 | Kraus et al. | |
| 5,129,890 A | 7/1992 | Bates et al. | |
| 5,188,621 A | 2/1993 | Samson | |
| 5,222,949 A | 6/1993 | Kaldany | |
| 5,238,004 A | 8/1993 | Sahatjian et al. | |
| 5,267,574 A | 12/1993 | Viera et al. | |
| 5,313,967 A | 5/1994 | Lieber et al. | |
| 5,372,144 A | 12/1994 | Mortier et al. | |
| 5,406,960 A | 4/1995 | Corso, Jr. | |
| 5,415,178 A | 5/1995 | Hsi et al. | |
| 5,429,139 A | 7/1995 | Sauter | |
| 5,497,783 A | 3/1996 | Urick et al. | |
| 5,606,979 A | 3/1997 | Hodgson | |
| 5,606,981 A | 3/1997 | Tartacower et al. | |
| 5,664,580 A * | 9/1997 | Erickson et al. ............. | 600/585 |
| 5,772,609 A | 6/1998 | Nguyen et al. | |

(Continued)

FOREIGN PATENT DOCUMENTS

JP    58-90389    5/1983

(Continued)

OTHER PUBLICATIONS

U.S. Appl. No. 10/346,698, filed Jan. 17, 2003, Art Miller et al.

*Primary Examiner*—Max Hindenburg
*Assistant Examiner*—Jeffrey G Hoekstra
(74) *Attorney, Agent, or Firm*—Crompton, Seager & Tufte, LLC

(57) ABSTRACT

An intracorporeal device includes a helically wound coil having a plurality of windings having an outer perimeter and forming a coil length and a plurality of joining elements disposed on only a portion of the outer perimeter and along the coil length. Each joining element couples two coil windings.

43 Claims, 3 Drawing Sheets

U.S. PATENT DOCUMENTS

| | | |
|---|---|---|
| 5,797,856 A | 8/1998 | Frisbie et al. |
| 5,830,155 A | 11/1998 | Frechette et al. |
| 5,882,333 A | 3/1999 | Schaer et al. |
| 5,891,055 A | 4/1999 | Sauter |
| 5,931,830 A | 8/1999 | Jacobsen et al. |
| 5,951,496 A | 9/1999 | Willi |
| 5,984,878 A | 11/1999 | Engleson |
| 6,022,343 A | 2/2000 | Johnson et al. |
| 6,027,863 A | 2/2000 | Donadio, III |
| 6,056,702 A | 5/2000 | Lorenzo |
| 6,061,595 A | 5/2000 | Safarevich |
| 6,152,912 A | 11/2000 | Jansen et al. |
| 6,296,616 B1 | 10/2001 | McMahon |
| 6,312,458 B1 | 11/2001 | Golds |
| 6,373,024 B1 | 4/2002 | Safarevich et al. |
| 6,402,706 B2 | 6/2002 | Richardson et al. |
| 6,409,683 B1 | 6/2002 | Fonseca |
| 6,508,803 B1 | 1/2003 | Horikawa et al. |
| 6,527,732 B1 | 3/2003 | Strauss et al. |
| 6,544,197 B2 | 4/2003 | DeMello |
| 6,599,254 B2 | 7/2003 | Winters |
| 6,849,224 B2 | 2/2005 | Wang et al. |
| 7,074,197 B2 | 7/2006 | Reynolds et al. |
| 7,182,735 B2 | 2/2007 | Shireman et al. |
| 7,303,533 B2 | 12/2007 | Johansen et al. |
| 2001/0009980 A1 | 7/2001 | Richardson et al. |
| 2002/0049392 A1 | 4/2002 | DeMello |
| 2003/0018318 A1 | 1/2003 | Melsky |
| 2003/0069520 A1 | 4/2003 | Skujins et al. |
| 2003/0069521 A1 | 4/2003 | Reynolds et al. |
| 2003/0149465 A1 | 8/2003 | Heidner et al. |
| 2004/0167442 A1 | 8/2004 | Shireman et al. |

FOREIGN PATENT DOCUMENTS

| | | |
|---|---|---|
| JP | 59-92188 | 5/1984 |
| JP | 2001229985 | 8/2001 |
| WO | 2004091440 | 10/2004 |

\* cited by examiner

MEDICAL DEVICE COIL

TECHNICAL FIELD

The invention pertains generally to medical device coils useful for a variety of applications such as in guidewires, catheters, and the like.

BACKGROUND

A wide variety of medical devices such as catheters and guidewires have been developed. Medical devices such as guidewires can be used in conjunction with devices such as catheters to facilitate navigation through the anatomy of a patient. Because the anatomy of a patient may be very tortuous, it can be desirable to have particular performance features in an elongate medical device. A number of different structures and assemblies for elongate medical devices such as guidewires are known each having certain advantages and disadvantages. However, there is an ongoing need to provide alternative structures and assemblies.

SUMMARY OF SOME EMBODIMENTS

The invention provides several alternative designs, materials and methods of manufacturing alternative medical device structures and assemblies.

Accordingly, an example embodiment of the invention can be found in an intracorporeal device that includes a helically wound coil having a plurality of windings having an outer perimeter and forming a coil length and a plurality of joining elements disposed on only a portion of the outer perimeter and along the coil length. Each joining element couples two or more coil windings.

Another example embodiment of the invention can be found in an intracorporeal device including a helically wound coil having a plurality of windings forming a coil length and four joining elements disposed along the coil length. Each joining element couples two or more coil windings.

Another example embodiment of the invention can be found in an intracorporeal device including a helically wound coil having a plurality of windings forming a coil length and a plurality of joining elements disposed along the coil length. Each joining element only couples two or more coil windings.

Another example embodiment of the invention can be found in a medical device including an elongate shaft, a helically wound coil having a plurality of windings having an outer perimeter and forming a coil length disposed about a portion of the elongate shaft, and a plurality of joining elements disposed on only a portion of the outer perimeter and along the coil length. Each joining element couples two or more coil windings.

Another example embodiment of the invention can be found in a guidewire including an elongate shaft having a proximal end and an opposing distal end, a helically wound coil having a plurality of windings having an outer perimeter and forming a coil length disposed about a portion of the distal end, and a plurality of joining elements disposed on only a portion of the outer perimeter and along the coil length. Each joining element couples two or more coil windings.

Another example embodiment of the invention can be found in a guidewire including an elongate shaft having a proximal end and an opposing distal end, a helically wound coil having a plurality of windings having an outer perimeter and forming a coil length disposed about a portion of the distal end, and a plurality of joining elements disposed on only a portion of the outer perimeter and along the coil length. Each joining element couples two coil windings. A second coil has a plurality of windings circumferentially disposed about the first coil. The joining elements couple a plurality of second coil windings to adjacent first coil windings.

Another example embodiment of the invention can be found in a process for forming and intracorporeal device including forming a plurality of joining elements on a helically wound coil having a plurality of windings that define an outer perimeter and form a coil length. The joining elements are disposed on only a portion of the outer perimeter and along the coil length and each joining element couples two or more coil windings.

The above summary of some embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
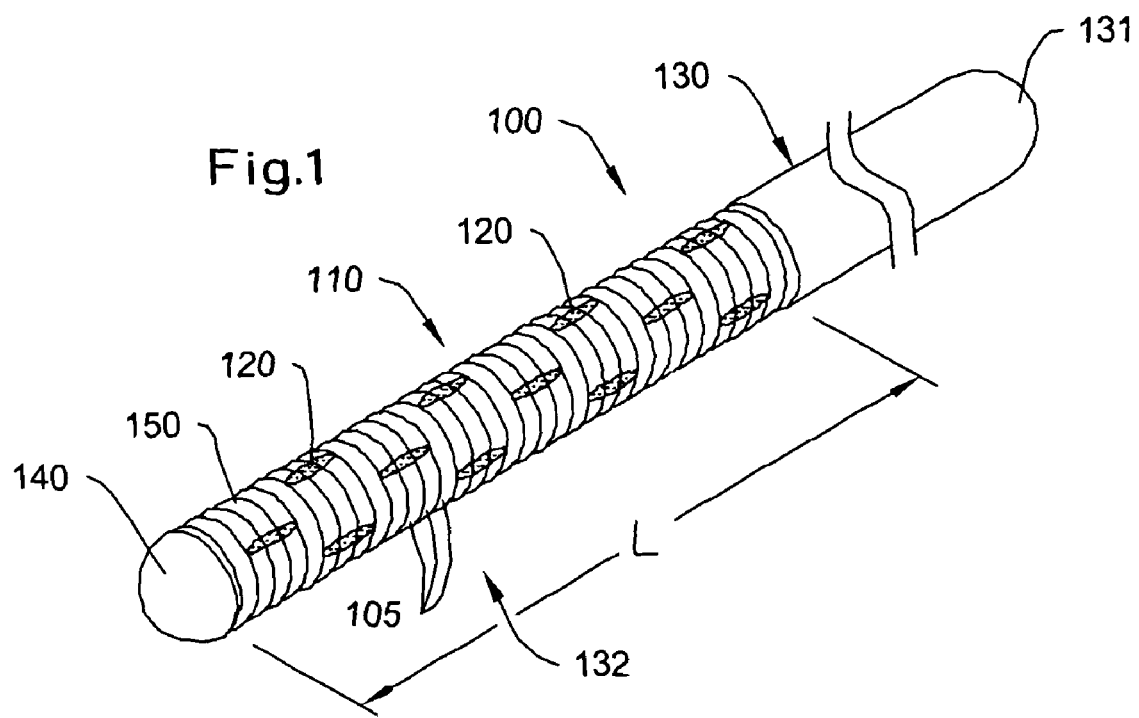
FIG. 1 is a perspective view of an example coil with a plurality of joining elements, incorporated into an elongate medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention. For example, although discussed with specific reference to guidewires in the particular embodiments described herein, the invention may be applicable to a variety of medical devices that are adapted to be advanced into the anatomy of a patient through an opening or lumen. For example, the invention may be applicable to fixed wire devices, catheters (e.g. guide, balloon, stent delivery, etc.), drive shafts for rotational devices such as atherectomy catheters and IVUS catheters, endoscopic devices, laparoscopic devices, embolic protection devices, spinal or cranial navigational devices, and other such devices. Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

Refer now to FIG. 1, which is a perspective view of a coil 110 with a plurality of joining elements 120, incorporated into an elongate medical device 100. The elongate medical device 100 may include an elongate shaft or core 130. The elongate shaft or core 130 can have a proximal end 131 and an opposing distal end 132. The coil 110 can be disposed on a portion of the elongate shaft, for example, at the distal end 132. A distal tip 140 can be disposed on an end of the coil 110 and/or the elongate shaft or core 130. The coil 110 may have a plurality of windings 105 that form a coil length L.

The coil 110 can be formed of a variety of materials including metals, metal alloys, polymers, and the like. Some examples of material for use in the coil 110 include a metal or a metal alloy such as a stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. Some additional examples of suitable material include a polymer material, such as a high performance polymer.

In some embodiments, the coil 110 or portions thereof can be made of, or coated or plated with, or otherwise include a radiopaque material. Radiopaque materials are understood to be materials capable of producing a relatively bright image on a fluoroscopy screen or another imaging technique during a medical procedure. This relatively bright image aids the user of medical device 100 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, the coil 110, or other portions of the device 100, can include materials or structure to impart a degree of MRI compatibility. For example, to enhance compatibility with Magnetic Resonance Imaging (MRI) machines, it may be desirable to make the coil 110, or other portions of the medical device 100, in a manner that would impart a degree of MRI compatibility. For example, the elongate shaft or core 130, the coil 110, or portions thereof, or other portions of the device 100, may be made of a material that does not substantially distort the image and create substantial artifacts (artifacts are gaps in the image). Certain ferromagnetic materials, for example, may not be suitable because they may create artifacts in an MRI image. The elongate shaft or core 130, the coil 110, or portions thereof, may also be made from a material that the MRI machine can image. Some materials that exhibit these characteristics include, for example, tungsten, Elgiloy, MP35N, nitinol, and the like, and others, or combinations or alloys thereof.

In some embodiments, the coil 110 can be made of a material that is compatible with the core wire 130 and the distal tip 140. The particular material used can be chosen in part based on the desired flexibility requirements or other desired characteristics. In some particular embodiments, the coil 110 can be formed from a superelastic or linear elastic nickel-titanium alloy, for example, linear elastic or superelastic nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Within the family of commercially available nitinol alloys, is a category designated "super elastic" (i.e. pseudoelastic) and a category designated "linear elastic". Although these two categories of material are similar in chemistry, they each exhibit distinct and useful mechanical properties. Either, or both superelastic and linear elastic nitinol can be used.

One example of a suitable nickel-titanium alloy that may exhibit linear elastic properties is FHP-NT alloy commercially available from Furukawa Techno Material Co. of Kanagawa, Japan. Some examples of suitable nickel-titanium alloys that may exhibit linear elastic characteristics include those disclosed in U.S. Pat. Nos. 5,238,004 and 6,508,803, which are incorporated herein by reference.

The coil 110 can be formed of round or flat ribbon ranging in dimensions to achieve the desired flexibility. It can also be appreciated that other cross-sectional shapes or combinations of shapes may be utilized without departing from the spirit of the invention. For example, the cross-sectional shape of wires or filaments used to make the coil may be oval, rectangular, square, triangle, polygonal, and the like, or any suitable shape. In some embodiments, the coil 110 can be a round ribbon in the range of about 0.001-0.015 inches in diameter, and can have a length in the range of about 0.1 to about 20 inches, however, other dimensions are contemplated.

The coil 110 can be wrapped in a helical fashion by conventional winding techniques. The pitch of adjacent turns of the coil 46 may be tightly wrapped so that each turn touches the succeeding turn or the pitch may be set such that the coil 110 is wrapped in an open fashion.

A plurality of joining elements 120 can be disposed along the coil length L. The joining elements couple a plurality of coil windings 105 together. Each joining element 105 may join from 2, 3, 4, 5, 6, 7, 8, 9, or 10 or more coil windings 105 together. There may be 2, 3, 4, 5, 6, 7, 8, 9, 10, 11, 12, 13, 14, 15, 16, 17, 18, 19, 20, 25, 30, 35, 40 or more joining elements 120 disposed in a uniform or non-uniform pattern along the coil length. In at least some embodiments, the joining elements 120 may only function to join coil windings 105 together. For example, in at least some embodiments, the coil joining element or elements 120 join a plurality of coil windings 105 together, but do not act to join any other structure within the device 100. In such embodiments, the coil joining element or elements 120 act only to join coil windings 105 together, and do not join any other structure to the coil. For example, in some such embodiments, the joining elements 120 do not join the coil 110 to the shaft or core 130.

The joining elements 120, by interconnecting a series of coil windings, can provide enhanced torque transmission along the coil length L and/or enhanced push-ability while still providing flexibility that a coil 110 offers. The degree of enhanced torque transmission and/or push-ability is dependent at least in part on the number of joining elements along the length of the coil, and the size of each joining element (i.e. the number of coil windings joined be each joining element). Those of skill in the art, and others will recognize that as a general proposition, that greater enhanced torque transmission and/or push-ability can be achieved by using a greater the number of joining elements along a coil length, and/or by increasing the number of coil windings 105 joined by each joining element 120. The number and size of the joining elements 120 can be varied to obtain the desired characteristics.

In some embodiments, the joining elements 120 may have a length in the range of about 0.1 to about 1.5 mm and a width in the range of about 0.1 to about 0.5 mm. The joining elements 120 can be discrete elements aligned orthogonal to the coil windings 105 as illustrated in FIG. 1. The joining elements 120 may be formed of a material the same as or different from the coil 110. The coil windings 105 define an outer perimeter 150. The joining elements 120 can be disposed about the outer perimeter 150 such that only a portion of the outer perimeter 150 is covered by joining elements 120. In some embodiments, each joining element 120 may be disposed on less than 1/10 of the total outer perimeter 150 of each winding 105.

The joining elements 120 can be formed in any suitable manner, including for example welding, soldering, brazing, adhesive bonding, mechanical interlocking and the like. It is to be appreciated that various welding processes can be utilized without deviating from the spirit and scope of the invention. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, micro plasma welding, electron beam, and friction or inertia welding.

In laser welding, a light beam is used to supply the necessary heat. Laser welding can be beneficial in the processes contemplated by the invention, as the use of a laser light heat source can provide pinpoint accuracy. In some embodiments, laser diode soldering can be useful.

The joining elements 120 can be created or disposed on the coil 110 prior to the attachment of the coil 110 to other structure of the device 100, or in some embodiments, can be created or disposed on the coil 110 after attachment of the coil to other structure of the device, such as the core or shaft 130 or the distal tip 140.

Such a coil 110, including joining elements, as discussed above, can be incorporated into a broad variety of medical devices. For example, as shown in FIG. 1, the coil 110 can be incorporated into an elongate medical device 100, such as a guidewire, that may include an elongate shaft or core 130. The coil 110 can be disposed on a portion of the elongate shaft, for example, at the distal end 132. It should be understood, however, that such a coil, including joining elements 120, can be incorporated into a broad variety of medical devices.

With reference to the embodiment shown in FIG. 1, the elongate shaft or core 130 can have a solid cross-section or a hollow cross-section. In other embodiments, the elongate shaft or core 130 can include a combination of areas having solid cross-sections and hollow cross sections. Moreover, the elongate shaft or core 130 can be made of rounded wire, flattened ribbon, or other such structures having various cross-sectional geometries. The cross-sectional geometries along the length of the elongate shaft or core 130 can also be constant or can vary. For example, FIG. 1 depicts the elongate shaft or core 130 as having a generally round cross-sectional shape. It can be appreciated that other cross-sectional shapes or combinations of shapes may be utilized without departing from the spirit of the invention. For example, the cross-sectional shape of the elongate shaft or core 130 may be oval, rectangular, square, polygonal, and the like, or any suitable shape.

In some embodiments, the elongate shaft or core 130 can be formed of any suitable metallic, polymeric or composite material. In some embodiments, part or all of the elongate shaft or core 130 can be formed of a metal or a metal alloy such as a stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. The particular material used can be chosen in part based on the desired flexibility requirements or other desired characteristics or the elongate shaft or core 130. In some particular embodiments, the elongate shaft or core 130 can be formed from a superelastic or linear elastic nickel-titanium alloy, for example, linear elastic or superelastic nitinol, for example, those discussed above with regard to the coil 110.

The entire elongate shaft or core 130 can be made of the same material, or in some embodiments, can include portions or sections that are made of different materials. In some embodiments, the material used to construct different portions of the core wire 130 can be chosen to impart varying flexibility and stiffness characteristics to different portions of the wire. For example, a proximal portion 131 and a distal portion 130 can be formed of different materials (i.e., materials having different moduli of elasticity) resulting in a difference in flexibility. In some embodiments, the material used to construct the proximal portion 131 can be relatively stiff for push-ability and torque-ability, and the material used to construct the distal portion 132 can be relatively flexible by comparison for better lateral track-ability and steer-ability. For example, the proximal portion 131 can be formed of, for example, straightened 304v stainless steel wire, and the distal portion 132 can be formed of, for example, a straightened super elastic or linear elastic alloy (e.g., nickel-titanium) wire.

In embodiments where different portions of elongate shaft or core 130 are made of different material, the different portions can be connected using any suitable connecting techniques. For example, the different portions of the elongate shaft or core 130 can be connected using welding, soldering, brazing, adhesive, or the like, or combinations thereof. Additionally, some embodiments can include one or more mechanical connectors or connector assemblies to connect the different portions of the elongate shaft or core 130 that are made of different materials. The connector may comprise any structure generally suitable for connecting portions of a elongate shaft or core 130. One example of a suitable structure includes a structure such as a hypotube or a coiled wire which has an inside diameter sized appropriately to receive and connect the different portions of the elongate shaft or core 130. Some methods and structures that can be used to interconnect different shaft sections are disclosed in U.S. patent application Ser. Nos. 09/972,276, and 10/086,992, which are incorporated herein by reference.

In at least some embodiments, portions or all of the elongate shaft or core 130, the coil 110, or other structures included within the medical device 100 may also be doped with, coated or plated with, made of, or otherwise include a radiopaque material. Additionally, in some embodiments, a degree of MRI compatibility can be imparted into the medical device 100, as discussed above.

The elongate shaft or core 130 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of the elongate shaft or core 130 may be tapered and the taper can be in either the proximal or the distal direction. The number, arrangement, size, and length of the tapering and constant diameter portions can be varied to achieve the desired characteristics, such as flexibility and torque transmission characteristics.

The distal tip 140 can be formed from a variety of different materials, depending on desired performance characteristics. In some embodiments, the distal tip can form an atraumatic portion on the distal end of the device 100. In some embodiments, the distal tip 140 can be formed of a material such as a metallic material that is amenable to being welded, soldered, or otherwise attached to the distal end 132 of the elongate shaft or core 130. For example, in some embodiments, the distal tip 140 can be a solder tip that is disposed via soldering at the distal end of the device and forms an atraumatic rounded portion. In other embodiments, the distal tip can be prefabricated, or partially prefabricated, structure that is thereafter attached to the distal end of the device using suitable attachment techniques, such as welding, soldering, brazing, crimping, friction fitting, adhesive bonding, mechanical interlocking and the like. A variety of different processes, such as soldering, deep drawing, roll forming or metal stamping, metal injection molding, casting and the like, can be used to form the distal tip 140.

In some embodiments, it may be beneficial, but not always necessary, that the distal tip 140 to be formed of a material that is compatible with the particular joining technique used to connect the tip 140 to the other structure. For example, in some particular embodiments, it can be beneficial but not necessary for the distal tip 140 to be formed of the same metal or metal alloy as the distal end 132 of the elongate shaft or core 130. For example, if the elongate shaft or core 130 is formed of stainless steel, it can be beneficial for the distal tip 140 to be formed of stainless steel. In other embodiments, both of the distal tip 140 and the distal end 132 of the elongate shaft or core 130 can be formed of the same metal alloy, such as nitinol.

To form the assembly 100 shown in FIG. 1, the coil 110 can be positioned proximate the elongate shaft or core 130 as illustrated. The coil 110 can be secured to the elongate shaft or core 130 in any suitable manner, including for example welding, soldering, brazing, crimping, friction fitting, adhesive bonding, mechanical interlocking and the like. In the embodiment shown, the coil 110 can be secured at its proximal end to the elongate shaft or core 130 at a proximal attachment point 131, and can be secured at its distal end to the elongate shaft or core 130 via the distal tip 140. In some embodiments, the distal tip 140 is a solder tip or a weld tip that is soldered or welded to the elongate shaft or core 130 and the coil 110, and forms an atraumatic tip. In other embodiments, the distal tip 140 is prefabricated, or partially prefabricated, and is connected to the elongate shaft or core 130 and the coil 110 using a suitable attachment technique.

In some embodiments, the coil 110 and/or the distal tip can be welded to the elongate shaft or core 130. It is to be appreciated that various welding processes can be utilized without deviating from the spirit and scope of the invention. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment that may be suitable in some embodiments is commercially available from Unitek Miyachi of Monrovia, Calif. and Rofin-Sinar Incorporated of Plymouth, Mich. Resistance welding equipment that may be useful in some embodiments is commercially available from Palomar Products Incorporated of Carlsbad, Calif. and Polaris Electronics of Olathe, Kans. TIG welding equipment that may be useful in some embodiments is commercially available from Weldlogic Incorporated of Newbury Park, Calif. Microplasma welding equipment that may be useful in some embodiments is commercially available from Process Welding Systems Incorporated of Smyrna, Tenn.

In some embodiments, laser or plasma welding can be used to secure the distal tip 140, the coil 110 and the elongate shaft or core 130 securely together. In laser welding, a light beam is used to supply the necessary heat. Laser welding can be beneficial in the processes contemplated by the invention, as the use of a laser light heat source can provide pinpoint accuracy. In some embodiments, laser diode soldering can be useful. As indicated above, the joining elements 120 can be created on the coil 110 either prior to the attachment of the coil 110 to the distal tip 140 and the elongate shaft or core 130, or after attachment.

It should also be understood that the device 100 can include additional structure, such as shaping ribbons, marker bands and or coils, additional inner or outer coils, inner or outer sheaths, and the like. Those of skill in the art and others will recognize how to incorporate such additional structures into the device, as is generally known.

Figure 2:
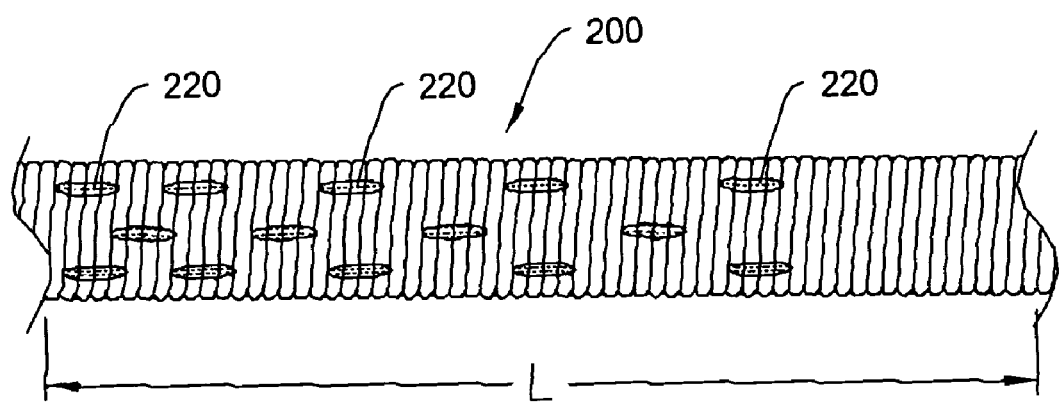
FIG. 2 is a side elevation view of an example coil with a plurality of joining elements.

FIG. 2 is a side elevation view of another example embodiment of a coil 200 including a plurality of joining elements 220. In this embodiment, the plurality of joining elements 220 forms a pattern along the coil length L such that the density of joining elements 220 along the length of the coil changes. This plurality of joining elements 220 has a density of joining elements 220 per unit length that decreases along the coil length L as illustrated in FIG. 2. Decreasing the density of joining elements 220 per unit along the coil length L provides the ability to modify flexibility, torque transmission and pushability as a function of position along the coil length L. For example, a higher density of joining elements 220 at a proximal end of the coil can provide a coil 200 with high torque transfer at the proximal end and high flexibility at a distal end of the coil 200. It should be understood that this is only one example embodiment, and that the density of joining elements 220 per unit along the coil length L can be modified, for example such that the density is higher near the distal end, or such that the density is higher near the middle of the coil, or such that the density varies along the length of the coil, and the like.

Figure 3:
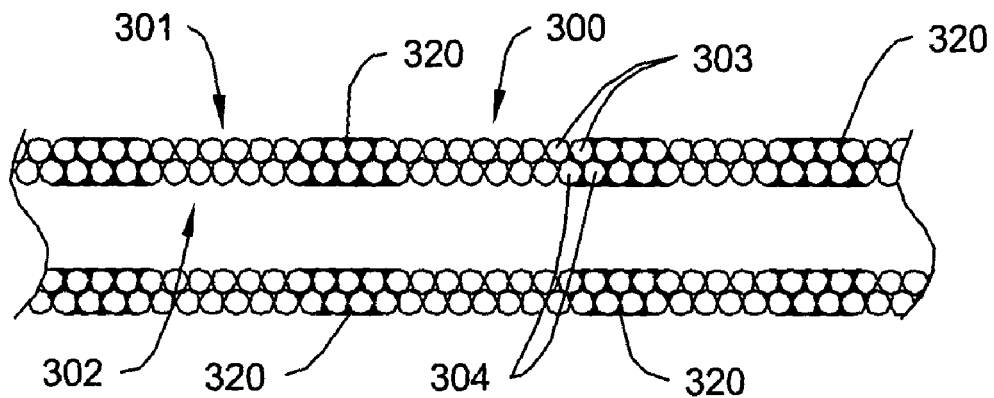
FIG. 3 is a cross-sectional view of an example of overlapping coils with a plurality of joining elements.

FIG. 3 is a cross-sectional view of over-lapping coils 300 with a plurality of joining elements in accordance with the invention. An outer coil 301 can be circumferentially disposed over a portion of an inner coil 302. The outer coil 301 may be formed of the same or different material as the inner coil 302. The joining elements 320 couple a plurality of inner core windings 304 to a plurality of outer core windings 303. The joining elements 320 can be disposed on the inner coil 302 and outer coil 301 in a manner consistent with that described above.

Figure 4:
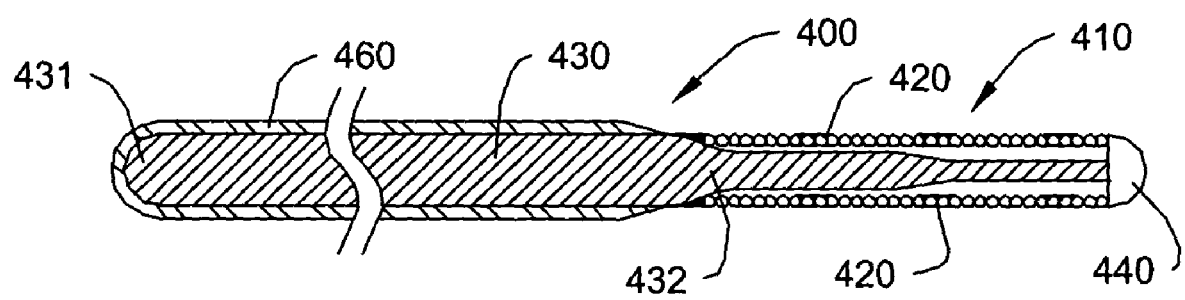
FIG. 4 is a cross-sectional view of an example guidewire with a coil with a plurality of joining elements.

FIG. 4 is a cross-sectional view of the guidewire 400 with a coil 410 with a plurality of joining elements 420 in accordance with the invention. The guidewire 400 includes a core 430. The core may have a proximal section 431 and an opposing distal section 432. The distal section 432 can include a series of taper and constant diameter sections as illustrated in FIG. 4. In other embodiments, the proximal section 431 may also include a series of taper and constant diameter sections. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of guidewire 400 and/or guidewire sections 431/432 may be tapered and the taper can be in either the proximal or the distal direction. In some other embodiments, a guidewire core wire can have a profile in which the core wire has a greater number of constant diameter sections, separated by a greater number of taper sections. In some embodiments, a guidewire core wire can have fewer or no tapers. The tapers can be as illustrated in FIG. 4, or they can be longer (more gradual), or shorter (less gradual).

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. Some examples of suitable grinding methods are disclosed in U.S. patent application Ser. No. 10/346,698 filed Jan. 17, 2003, which is herein incorporated by reference. The narrowing and constant diameter portions as shown in FIG. 4 are not intended to be limiting, and alterations of this arrangement can be made without departing from the spirit of the invention. One of skill will recognize that a guidewire core wire can have a profile different from that illustrated in FIG. 4.

The coil 410 can be disposed about a portion of the core distal section 432. The coil 410 can have a plurality of joining elements 420 as described above. The core 430 can be formed from a variety of materials as described above. The coil can be disposed between the core 430 and a distal tip 440 and constructed as described above.

A guidewire in accordance with some embodiments of the invention can optionally include a coating layer 460 such as a lubricious coating layer over part or all of the guidewire assembly 400 or even over part. Hydrophobic coatings such as fluoropolymers provide a dry lubricity which improves guide wire handling and device exchanges. Lubricious coatings improve steer-ability and improve lesion crossing capability. Suitable lubricious polymers are well known in the art and may include hydrophilic polymers such as polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion 432 of the guidewire is coated with a hydrophilic polymer and the more proximal portion 431 is coated with a fluoropolymer 460, such as polytetrafluoroethylene (PTFE).

Figure 5:
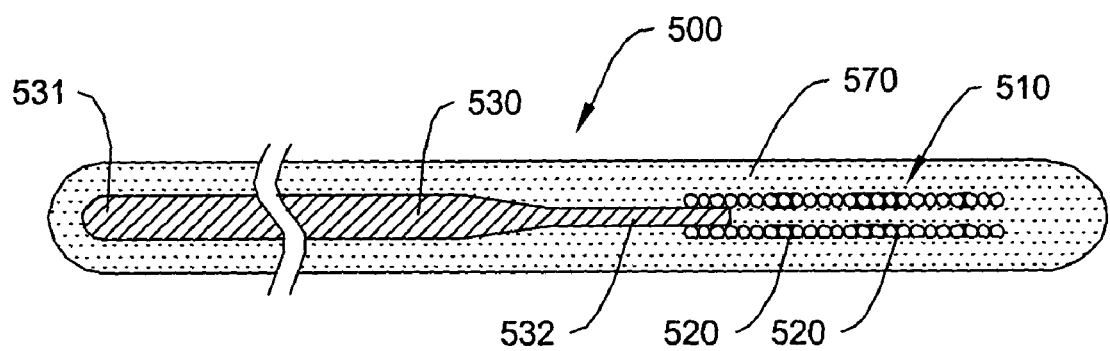
FIG. 5 is a cross-sectional view of an alternative example of a guidewire with a coil with a plurality of joining elements.

FIG. 5 is a cross-sectional view of the alternative guidewire 500 with a coil 510 with a plurality of joining elements 520 in accordance with the invention. The coil 510 is disposed over a portion of the core 530 and a polymer sheath or sleeve 570 is disposed over the core 530 and coil 510.

In this embodiment a polymer tip guidewire 500 is formed by including the polymer sheath or sleeve 570 that forms a rounded tip over the coil 510. The polymer sheath or sleeve 570 can be made from any material that can provide the desired strength, flexibility or other desired characteristics.

The use of a polymer can serve several functions, such as improving the flexibility properties of the guidewire assembly. Choice of polymers for the sheath or sleeve 570 will vary the flexibility of the guidewire. For example, polymers with a low durometer or hardness will make a very flexible or floppy tip. Conversely, polymers with a high durometer will make a tip which is stiffer. The use of polymers for the sleeve can also provide a more atraumatic tip for the guidewire. An atraumatic tip is better suited for passing through fragile body passages. Finally, a polymer can act as a binder for radiopaque materials, as discussed in more detail below.

Some suitable materials include polymers, and like material. Examples of suitable polymer material include any of a broad variety of polymers generally known for use as guidewire polymer sleeves. In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. By employing careful selection of materials and processing techniques, thermoplastic, solvent soluble and thermosetting variants of these materials can be employed to achieve the desired results.

Further examples of suitable polymeric materials include but are not limited to poly(L-lactide) (PLLA), poly(D,L- lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamide, poly(hydroxyethyl methacrylate), polyurethane, polysiloxane and their copolymers.

In some embodiments, the sheath or sleeve 570, or portions thereof, can include, or be doped with, radiopaque material to make the sheath or sleeve 570, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the sheath or sleeve 570 can include a distal section having a higher level of radiopaque material loading, and a proximal section having a correspondingly lower level of loading.

In some embodiments, it is also contemplated that a separate radiopaque member or a series of radiopaque members, such as radiopaque coils, bands, tubes, or other such structures could be attached to the guidewire core wire 530, or incorporated into the core wire by plating, drawing, forging, or ion implantation techniques.

The sheath or sleeve 570 can be disposed around and attached to the guidewire assembly 500 using any suitable technique for the particular material used. In some embodiments, the sheath or sleeve 570 can be attached by heating a sleeve of polymer material to a temperature until it is reformed around the guidewire assembly 500. In some other embodiments, the sheath or sleeve 570 can be attached using heat shrinking techniques. In other embodiments, the sheath or sleeve 570 can be co-extruded with the core wire 530. The sleeve 570 can be finished, for example, by a centerless grinding or other method, to provide the desired diameter and to provide a smooth outer surface.

Figure 6:
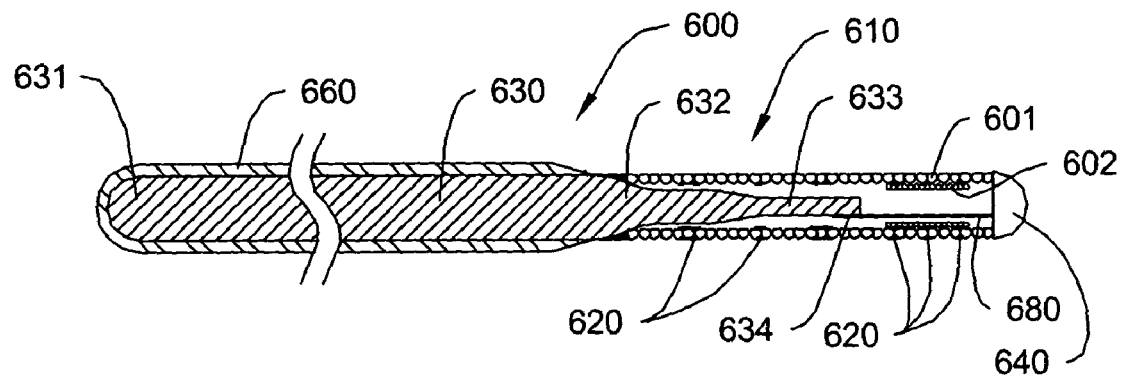
FIG. 6 is a cross-sectional view of an alternative guidewire with a coil with a plurality of joining elements.

FIG. 6 is a cross-sectional view of the alternative guidewire 600 with a coil 610 with a plurality of joining elements 620 in accordance with the invention. The guidewire 600 includes a core 630. The core may have a proximal section 631 and an opposing distal section 632. The distal section 632 can include a series of taper and constant diameter sections as illustrated in FIG. 6. The coil 610 can be disposed about a portion of the core distal section 632. The coil 610 can have a plurality of joining elements 620 as described above. The core 630 can be formed from a variety of materials as described above. The coil can be disposed between the core 630 and a distal tip 640 and constructed as described above. A wire or ribbon 680 can be disposed between the distal tip 640 and core 630. An inner coil 602 can be disposed adjacent to the outer coil 601 and coupled to each other with a plurality of joining elements 620 as described above.

The wire or ribbon 680 can be attached adjacent the distal end 632 of the core 630, and extend distally to the distal tip 640. In some embodiments, the wire or ribbon 680 can be a fabricated or formed wire structure, for example a coiled wires, as will be seen in embodiments discussed in more detail below. In the embodiment shown, the ribbon 680 is a generally straight wire that overlaps with and is attached to the constant diameter region 633 at attachment point 634. In some embodiments, the ribbon 680 overlaps with the constant diameter section 633 by a length in the range of about 0.05 to 1.0 inch, but in other embodiments, the length of the overlap can be greater or less.

The ribbon 680 can be made of any suitable material and sized appropriately to give the desired characteristics, such as strength and flexibility characteristics. Some examples of suitable materials include metals, metal alloys, polymers, and the like. In some embodiments, the ribbon 680 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire. The ribbon 680 can be attached using any suitable attachment technique. Some examples of attachment techniques include soldering, brazing, welding, adhesive bonding, crimping, or the like. In some embodiments, the ribbon or wire 680 can function as a shaping structure or a safety structure.

A guidewire 600 in accordance with some embodiments of the invention can optionally include a coating layer 660 such as a lubricious coating layer over part or all of the guidewire assembly 600 or even over part. Hydrophobic coatings such as fluoropolymers provide a dry lubricity which improves guide wire handling and device exchanges. Lubricious coatings improve steer-ability and improve lesion crossing capability. Suitable lubricious polymers are well known in the art and may include hydrophilic polymers such as polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion of the guidewire is coated with a hydrophilic polymer and the more proximal portion 631 is coated 660 with a fluoropolymer, such as polytetrafluroethylene (PTFE).

In some other embodiments, a guidewire core wire can have a profile in which the core wire has a greater number of constant diameter sections, separated by a greater number of taper sections. In some embodiments, a guidewire core wire can have fewer or no tapers. The tapers can be as illustrated in FIG. 6, or they can be longer (more gradual), or shorter (less gradual).

One of skill will recognize that a guidewire core wire can have a profile different from that illustrated in FIGS. 4, 5 and 6. For example, the core wire 430, 530, 630 can be continuously tapered, can have a tapered section or a number or series of tapered sections of differing diameters, or can have a constant diameter. In some embodiments, core wire 430, 530, 630 is tapered or otherwise formed to have a geometry that decreases in cross sectional area toward the distal end thereof. If tapered, core wire can include a uniform or a non-uniform transition of the sections, depending on the transition characteristics desired. For example, core wire may be linearly tapered, tapered in a curvilinear fashion, or tapered in a stepwise fashion. The angle of any such tapers can vary, depending upon the desired flexibility characteristics. The length of the taper may be selected to obtain a more (longer length) or less (shorter length) gradual transition in stiffness.

Similar to what is described above, the structure used to construct the core wire 430, 530, 630 can be designed such that a proximal portion 431, 531, 631 is relatively stiff for push-ability and torque-ability, and distal portion 432, 532, 632 is relatively flexible by comparison for better lateral track-ability and steer-ability. For example, in some embodiments, a proximal portion 431, 531, 631 has a constant or generally uniform diameter along its length to enhance stiffness. However, embodiments including a proximal portion 431, 531, 631 having a tapered portion or a series of tapered portions are also contemplated. The diameter of the proximal portion 431, 531, 631 can be sized appropriately for the desired stiffness characteristics dependent upon the material used. For example, in some embodiments, a proximal portion 431, 531, 631 can have a diameter in the range of about 0.010 to about 0.035 inches or greater, and in some embodiments, in the range of about 0.010 to about 0.018 inches or greater.

A distal portion 432, 532, 632 can likewise be constant diameter, can be continuously tapered, or can have a tapered section or a number or a series of tapered sections of differing diameters. In embodiments where the structure of core wire 430, 530, 630 is designed such that a distal portion 432, 532, 632 is relatively flexible by comparison to the proximal portion 431, 531, 631, the distal portion 432, 532, 632 can include at least one tapered or reduced diameter portion for better flexibility characteristics.

The lengths of the proximal portions 431, 531, 631 and distal portions 432, 532, 632 are typically, but not always, dictated by the length and flexibility characteristics desired in the final medical device. In some embodiments, the proximal portion 431, 531, 631 can have a length in the range of about 50 to about 300 centimeters, and the distal portion 432, 532, 632 can have a length in the range of about 3 to about 50 centimeters.

The core wire 430, 530, 630 can have a solid cross-section as shown, but in some embodiments, can have a hollow cross-section. In yet other embodiments, core wire 430, 530, 630 can include a combination of areas having solid cross-sections and hollow cross sections.

The tapered and constant diameter portions can be formed by any one of a number of different techniques, for example, by centerless grinding, stamping and the like. A centerless grinding technique can utilize an indexing system employing sensors (e.g., optical/reflective, magnetic) to avoid excessive grinding. In addition, the centerless grinding technique can utilize a CBN or diamond abrasive grinding wheel that is well shaped and dressed to avoid grabbing the core wire 430, 530, 630 during the grinding process.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

I claim:

1. An intracorporeal device comprising:
   a) a helically wound coil having a plurality of windings forming a coil length and defining a longitudinal coil axis extending along the coil length; and
   b) at least ten joining elements disposed along the coil length, wherein each joining element is located at a longitudinal position along the coil length relative to the coil axis and couples two or more coil windings, wherein a first series of joining elements are spaced apart longitudinally along the coil length, and a second series of joining elements are spaced apart longitudinally along the coil length, wherein the longitudinal positions of the joining elements in the first series are transversely offset from the longitudinal positions of the joining elements in the second series along the coil length, such that the joining elements in the first series are staggered relative to the joining elements in the second series along the coil length.

2. The intracorporeal device according to claim 1, wherein the joining elements form a non-uniform pattern along the coil length.

3. The intracorporeal device according to claim 2, wherein the joining elements have a density of joining elements per unit coil length that decreases along the coil length.

4. The intracorporeal device according to claim 3, wherein the density of joining elements per unit coil length decreases in the distal direction along the coil length.

5. The intracorporeal device according to claim 1, further comprising a third series of joining elements spaced apart longitudinally along the coil length, the third series of joining elements being transversely offset from the second series, wherein the joining elements of the first, second, and third series form a uniform pattern of joining elements along the coil length.

6. The intracorporeal device according to claim 1, wherein each joining element couples 3 to 10 coil windings.

7. The intracorporeal device according to claim 1, wherein each joining element is a discrete element aligned orthogonal to the windings.

8. The intracorporeal device according to claim 1, wherein each joining element is a discrete element having a width in the range of 0.1 to 0.5 mm and a length in the range of 0.1 to 1.5 mm.

9. An intracorporeal device comprising:
   a) a helically wound coil having a plurality of windings forming a coil length and defining a longitudinal coil axis extending along the coil length; and
   b) a plurality of joining elements disposed longitudinally along the coil length, wherein each joining element only couples two or more coil windings, and wherein a first joining element is longitudinally offset from a second joining element such that the first and second joining elements do not overlap longitudinally along the coil length as viewed from a direction transverse to the coil axis.

10. The intracorporeal device according to claim 9, wherein the plurality of joining elements includes at least 10 elements disposed along the coil length.

11. The intracorporeal device according to claim 9, wherein the plurality of joining elements form a non-uniform pattern of joining elements along the coil length.

12. The intracorporeal device according to claim 11, wherein the plurality of joining elements has a density of joining elements per unit coil length that decreases along the coil length.

13. The intracorporeal device according to claim 12, wherein the density of joining elements per unit coil length decreases in the distal direction along the coil length.

14. The intracorporeal device according to claim 9, wherein the plurality of joining elements form a uniform pattern of joining elements along the coil length.

15. The intracorporeal device according to claim 9, wherein each joining element couples 3 to 10 coil windings.

16. The intracorporeal device according to claim 9, wherein each joining elements is a discrete element aligned orthogonal to the windings.

17. The intracorporeal device according to claim 9, wherein each joining element is a discrete element having a width of 0.1 to 0.5 micrometer and a length of 0.1 to 1.5 mm.

18. An intracorporeal device comprising:
a) a helically wound coil having a plurality of windings having an outer perimeter and forming a coil length; and
b) a plurality of joining elements disposed on only a portion of the outer perimeter and along the coil length, wherein each joining element couples two or more coil windings, wherein the plurality of joining elements are disposed on the outer perimeter in a series of circumferential rings, each ring being spaced longitudinally from adjacent rings, each ring having one or more joining element spaced apart around the circumference of the coil, wherein the joining elements in each ring are substantially aligned longitudinally, and wherein of the joining elements of a first ring are circumferentially offset from joining elements of a second ring.

19. The intracorporeal device according to claim 18, wherein the plurality of joining elements includes at least 10 elements disposed along the coil length.

20. The intracorporeal device according to claim 18, wherein the plurality of joining elements form a non-uniform pattern of joining elements along the coil length.

21. The intracorporeal device according to claim 20, wherein the plurality of joining elements has a density of joining elements per unit coil length that decreases along the coil length.

22. The intracorporeal device according to claim 18, wherein the plurality of joining elements form a uniform pattern of joining elements along the coil length, with first, third, and further odd numbered rings having joining elements aligned longitudinally, and second, fourth, and further even numbered rings having joining elements aligned longitudinally.

23. The intracorporeal device according to claim 18, wherein each joining element couples 3 to 10 coil windings.

24. The intracorporeal device according to claim 18, wherein each joining element is a discrete element aligned orthogonal to the windings.

25. The intracorporeal device according to claim 18, wherein each joining element is a discrete element having a width of 0.1 to 0.5 mm and a length of 0.1 to 1.5 mm.

26. The intracorporeal device according to claim 18, wherein each joining element is disposed on less than 1/10 of the outer perimeter of each winding.

27. A medical device comprising:
a) an elongate shaft having a proximal end and a distal end;
b) a helically wound coil having a plurality of windings having an outer perimeter and forming a coil length disposed about a portion of the distal end of the elongate shaft; and
c) a plurality of joining elements disposed on only a portion of the outer perimeter and along the coil length, wherein each joining element couples two or more coil windings, and wherein the plurality of joining elements are disposed in two or more series, wherein the joining elements of each series are spaced apart along a longitudinal line, and the joining elements of adjacent series do not overlap longitudinally.

28. The medical device according to claim 27, wherein the plurality of joining elements includes 10 elements disposed along the coil length.

29. The medical device according to claim 27, wherein the plurality of joining elements form a non-uniform joining element pattern along the coil length.

30. The medical device according to claim 29, wherein the plurality of joining elements has a density of joining elements per unit coil length that decreases along the coil length.

31. The medical device according to claim 27, wherein the plurality of joining elements form a uniform joining element pattern along the coil length.

32. The medical device according to claim 27, wherein each joining element couples 3 to 10 coil windings.

33. The medical device according to claim 27, wherein each joining element is a discrete element aligned orthogonal to the windings.

34. The medical device according to claim 27, wherein each joining element is a discrete element having a width of 0.1 to 0.5 mm and a length of 0.1 to 1.5 mm.

35. A guidewire comprising:
a) an elongate shaft having a proximal end and an opposing distal end;
b) a helically wound coil having a plurality of windings having an outer perimeter and forming a coil length disposed about a portion of the distal end; and
c) a plurality of joining elements disposed on only a portion of the outer perimeter and along the coil length, wherein each joining element couples two coil windings, and wherein the plurality of joining elements are spaced apart along a plurality of longitudinal lines, wherein joining elements in adjacent lines have no longitudinal overlap.

36. The guidewire device according to claim 35, wherein the plurality of joining elements includes 10 elements disposed along the coil length.

37. The guidewire device according to claim 35, wherein the plurality of joining elements form a non-uniform joining element pattern along the coil length.

38. The guidewire device according to claim 37, wherein the plurality of joining elements has a density of joining elements per unit coil length that decreases along the coil length.

39. The guidewire device according to claim 35, wherein the plurality of joining elements form a uniform joining element pattern along the coil length.

40. The guidewire device according to claim 35, wherein each joining element couples 3 to 10 coil windings.

41. The guidewire device according to claim 35, wherein each joining element is a discrete element aligned orthogonal to the windings.

42. The guidewire device according to claim 35, wherein each joining element is a discrete element having a width of 0.1 to 0.5 mm and a length of 0.1 to 1.5 mm.

43. The guidewire according to claim 38, wherein the helically wound coil has a proximal end and a distal end and where the density of joining elements per unit length decreases from the proximal end to the distal end.

* * * * *